United States Patent [19]

Andersson et al.

[11] 4,240,291
[45] Dec. 23, 1980

[54] FLOW METER

[75] Inventors: Roland J. E. Andersson, Bjärred; Lars-Göran Olsson, Löddeköpinge; Bengt G. Paulsson, Lund, all of Sweden

[73] Assignee: Gambro AB, Lund, Sweden

[21] Appl. No.: 958,390

[22] Filed: Nov. 7, 1978

[30] Foreign Application Priority Data

Nov. 9, 1977 [SE] Sweden .................. 7712642

[51] Int. Cl.³ ............................................ G01F 11/04
[52] U.S. Cl. ................................ 73/861.05; 73/239
[58] Field of Search ............... 73/194 R, 194 E, 228, 73/239

[56] References Cited

U.S. PATENT DOCUMENTS

| 1,799,875 | 4/1931 | Thompson . | |
| 2,772,664 | 12/1956 | Jones et al. | 73/239 |
| 3,344,667 | 10/1967 | Malby | 73/239 |
| 3,657,925 | 4/1972 | Gross | 73/239 |
| 3,662,598 | 5/1972 | Spencer | 73/194 |
| 4,089,220 | 5/1978 | Houlberg | 73/194 |
| 4,118,980 | 10/1977 | Debeaux | 73/194 |

Primary Examiner—Herbert Goldstein
Attorney, Agent, or Firm—Lerner, David, Littenberg & Samuel

[57] ABSTRACT

A flow meter is provided for measuring the flow rate of fluid through a conduit having an inlet and an outlet, which includes a measuring chamber having a float disposed therein for movement in response to fluid flow, and a detector for detecting the movement of the float in the measuring chamber. Various devices are provided for controlling the path of fluid flow from the conduit outlet to the conduit inlet, which includes apparatus for allowing fluid to flow from the outlet through the measuring chamber in a first direction so as to move the float in the first direction past the detector, and for also allowing fluid to flow from the outlet through the measuring chamber in a second direction so as to move the float in the second direction past the detector. Apparatus is connected to the detector for measuring the rate of fluid flow in response to the movement of the float in the first and second directions.

19 Claims, 10 Drawing Figures

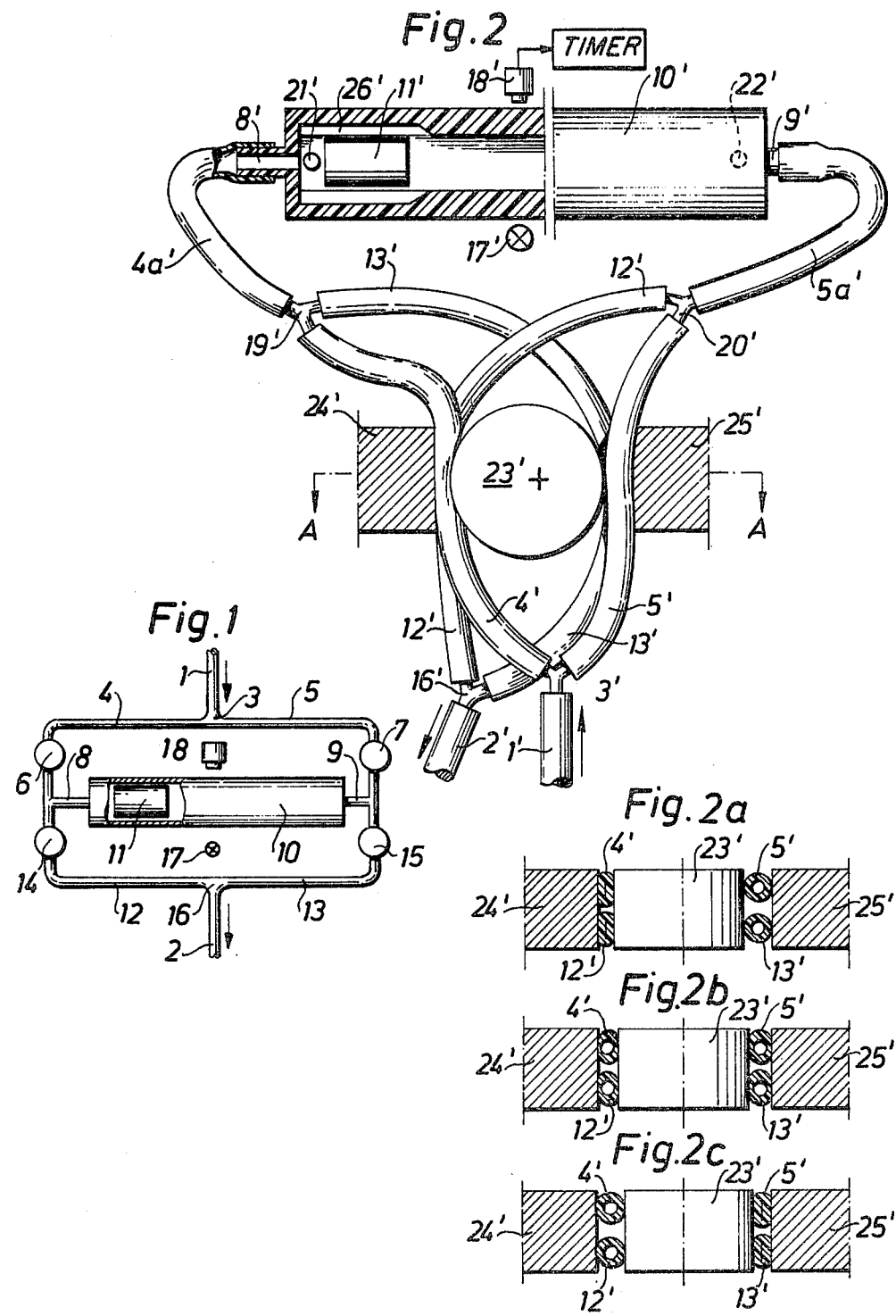

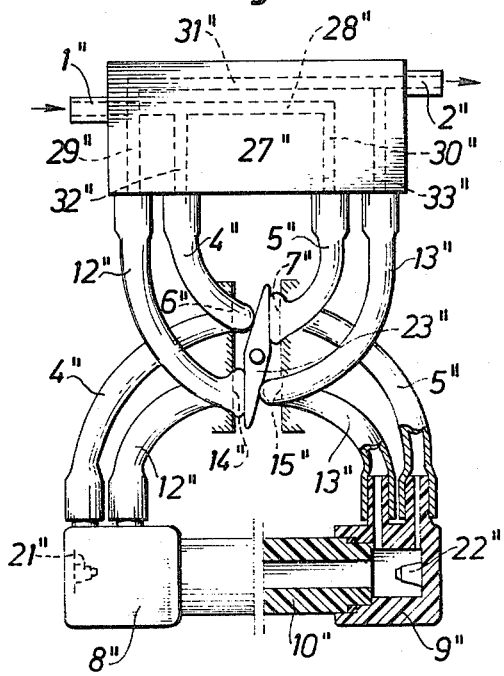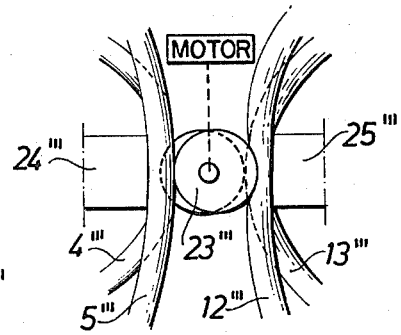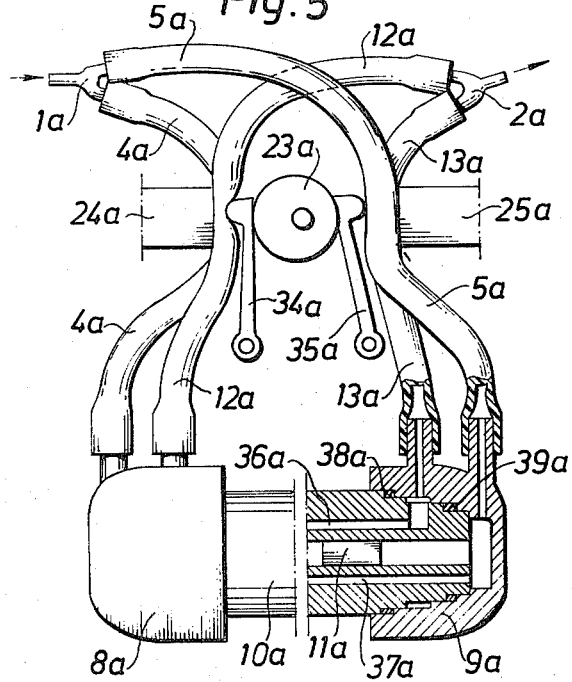

4,240,291

FLOW METER

FIELD OF THE INVENTION

The present invention relates generally to flow meters and to an improved flow meter which includes a measuring chamber having a float disposed therein for movement in response to fluid flow, which float is caused to move in opposite directions in order to determine the rate of fluid flow.

BACKGROUND OF THE INVENTION

Flow meters for measuring the rate of fluid flow are well known in the art. However, some of such flow meters are dependent on their position, that is, they must be placed horizontally or vertically in order to obtain a reading. In addition, some flow meters do not have the desired measuring accuracy. Further, in particular applications, it is desirable that a portion of the flow meter be disposable, especially in medical applications.

Accordingly, it is an object of the present invention to provide an improved flow meter which overcomes one or more of the aforesaid problems. Specifically, it is within the contemplation of the present invention to provide an improved flow meter which is not dependent upon its position to obtain a reading and is, at the same time, highly accurate.

It is a further object of the present invention to provide an improved flow meter which is simple to manufacture and has the advantage of being disposable so that it can be used in medical applications.

SUMMARY OF THE INVENTION

Briefly, in accordance with the principles of the present invention, an improved flow meter is provided for measuring the flow rate of fluid through a conduit, wherein the conduit has an inlet and an outlet. First and second flow paths are connected to the conduit outlet, and third and fourth flow paths are connected to the conduit inlet. In addition, a measuring chamber is provided having a float disposed therein for movement in response to fluid flow between first and second ports, and a detector is also provided for detecting the movement of the float in the measuring chamber. Operating means are also provided for alternately fluidly connecting the first port to the first and fourth flow paths and for alternately fluidly connecting the second port to the second and third flow paths. The present invention also includes means for controlling the path of fluid flow from the outlet to the inlet, which includes a device for actuating the operating means to a first position for allowing fluid to flow from the outlet through the first and third flow paths via the measuring chamber, while at the same time preventing the flow of fluid from the second flow path to the fourth flow path so as to move the float in a first direction past the detector. In addition, the device also actuates the operating means to a second position for preventing the flow of fluid from the first flow path to the third flow path, while at the same time allowing fluid to flow through the second and fourth flow paths via the measuring chamber so as to move the float in a second direction past the detector. Finally, apparatus is connected to the detector for measuring the rate of fluid flow in response to movement of the float in the first and second directions.

In a preferred embodiment, the fluid flow paths are formed of compressible tubes, with the operating means being employed to compress these tubes in order to control the path of fluid flow. Advantageously, compression of the fluid tubes avoids the introduction of any contamination into the system. This is especially important when the flow meter of the present invention is being used for medical applications, and it is desired to work under sterile conditions.

In the present invention, a particularly high degree of measuring accuracy is obtained if the specific gravity of the float is made to be substantially equal to that of the specific gravity of the liquid or fluid being measured. For example, this can be achieved by providing the float with a cylindrical shape with a core and shell having different specific gravities. In addition, the cylindrical shape of the float is particularly advantageous when the apparatus for reading the movement of the float is adapted to measure the time which it takes for the float to pass a point of measurement. In such case, at each end of the measuring chamber, stops may be provided so as to retain the float or measuring element for a short period of time before the movement of the float is reversed. Preferably, in the vicinity of the stops, the measuring chamber is provided with a larger cross-sectional area as compared to the cross-sectional area of the measuring chamber in the region where the actual measurement takes place. This insures that the liquid or fluid can flow past the float, so that the risk of having the float stick in the measuring chamber is reduced.

In a preferred embodiment, the measuring chamber is formed of a transparent tube which is provided with two end pieces with connectors for the first and second ports. Thus, the construction is very simple to manufacture. In addition, in obtaining the measurement, a simple photocell device can be employed.

BRIEF DESCRIPTION OF THE DRAWINGS

Further objects, features, and advantages of the present invention will become apparent upon the consideration of the following detailed description of presently preferred embodiments when taken in conjunction with the accompanying drawings, wherein:

FIG. 1 illustrates a first embodiment of the present invention in the form of a simple outline diagram;

FIG. 2 illustrates a second embodiment of the present invention;

FIGS. 2a to 2c illustrate cross-sectional views taken along the line A—A in FIG. 2 in three different operating positions;

FIG. 3 illustrates a third embodiment of the present invention;

FIG. 4 illustrates a double eccentric type of operating means which can be used instead of the operating means illustrated in FIGS. 2 and 3;

FIG. 5 shows another embodiment of the present invention;

FIG. 6b shows a modification of the embodiment of FIG. 6a.

DETAILED DESCRIPTION OF PREFERRED EMBODIMENTS OF THE INVENTION

Figure 6A:
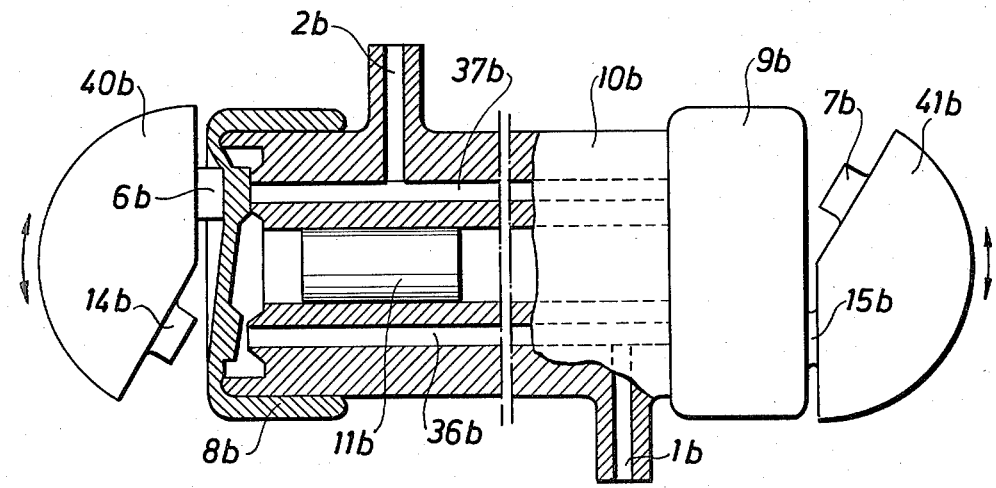
FIG. 6a illustrates a still further embodiment of the present invention.

In the outline diagram according to FIG. 1, the conduit in which the rate of flow is to be measured is designated 1, 2. The part of the conduit 1 is connected via a distributing point 3 to lines 4 and 5, respectively, which contain shut-off valves 6 and 7, respectively, and which are connected to the two inlets 8 and 9, respectively, of a measuring chamber 10. This measuring chamber contains a measuring element 11. The inlets 8 and 9 are connected further to lines 12 and 13 comprising shut-off valves 14 and 15, respectively, and which via a junction 16 are connected to the part of the conduit 2. When measurement is to take place, the shut-off valves 7 and 14, for example, are closed, while the valves 6 and 15 are kept open. The float 11 is then caused to float towards the right in FIG. 1, past a light source 17 and a photocell device 18, the output of which is supplied to suitable apparatus for measuring the rate of fluid flow. The photocell device 18 and such apparatus may measure, for example, the time it takes for the measuring element 11 to pass it. Directly after the measurement has been carried out, the direction of flow in the measuring chamber 10 is reversed by closing the valves 6 and 15, while at the same time, the valves 7 and 14 are opened. The movement of the measuring element 11 is thereby reversed so that it will be directed towards the left in FIG. 1. The float 11 again passes the light source 17, and the photocell device 18 and the measurement can be repeated.

The embodiment of the flow meter in accordance with the invention shown in FIG. 2 differs from that shown in FIG. 1 mainly in that it is made up of a number of single tubes, some coupling components and a measuring element in the form of an expendable part which may be discarded after use. In FIG. 2 the same reference designations have been used as in FIG. 1 for corresponding parts, but with the addition of a prime sign. Thus, the conduit wherein the velocity of flow is to be measured is designated 1', 2'. The part of conduit 1' is connected via a simple Y-junction 3' to tubes 4' and 5'. These tubes, in turn, are connected via junction pieces 19' and 20', respectively, to tubes 4a' and 5a'. These, in turn, open into the inlets 8' and 9', respectively, in a measuring chamber 10'. A measuring element 11' is movable between two stops 21' and 22', respectively.

The part of conduit 2' is connected via a Y-shaped junction piece 16' to tubes 12' and 13', respectively. These tubes are connected via junction pieces 20' and 19' to the tubes 4a' and 5a' and thus also to the inlets 8' and 9' of the measuring chamber 10'. The valves 6, 7, 14, and 15 in the construction in FIG. 1 are replaced here by an eccentric 23' and two seats 24' and 25', respectively. With the help of this eccentric 23', the tubes 4', 5', 12, and 13' can be compressed in pairs in such a manner as can be seen in detail in FIGS. 2a to 2c. In FIG. 2a, a position is shown in which both the tubes 4' and 12' are closed, while the tubes 5' and 13' are open. FIG. 2b shows a position wherein all four tubes are open. FIG. 2c finally shows a position in which the tubes 5' and 13' are closed, while tubes 4' and 12' are kept open. As shown in the drawings, any suitable apparatus may be utilized for actuating the eccentric 23'.

The function of the construction in accordance with FIG. 2 is substantially the same as that of the construction in accordance with FIG. 1. Thus, a reversible movement between the stops 21' and 22' is imparted to the float 11' by the eccentric 23'. At the stop 21', the measuring chamber 10' is provided with a widened part 26'. This allows the liquid measured to flow past the measuring element during a short period before the movement is reversed. A correspondingly widened part also exists at the other end of the measuring chamber 10' adjoining the stop 22'. This part, however, is not shown in the figure. Numerals 17' and 18', respectively, designate a schematically-indicated measuring arrangement in the form of a light source 17' and a photocell device 18'. It will be clear though to those versed in the art that other types of measuring arrangements can of course also be used for measuring the movement of the float.

As can best be seen from FIGS. 2a to 2c, the opening and closing of the tubes 4', 5', 12', and 13' takes place in such a manner that the total pressure drop through the tubes is practically constant.

In FIG. 3, a third embodiment of the subject of the invention is shown. This too is built up substantially according to the same principles as the constructions according to FIGS. 1 and 2. Corresponding parts have therefore been given the same reference designations but with the addition of a double prime sign. The liquid which is to be measured is thus introduced via a conduit section 1'' and withdrawn via a conduit section 2''. These conduit sections are connected to a coupling part 27'' with internal ducts 28'' to 33''. These ducts are connected to compressible tubes 4'', 5'', 12'', and 13'', respectively, which can be clamped together with the help of a rocker arm 23'' against four seats 6'', 7'', 14'', and 15''. In this way, precisely the same effect is achieved as with the help of the schematically-indicated valves 6, 7, 14, and 15 in the construction according to FIG. 1. Thus, a reversible movement can be imparted to a measuring element 11'' (not shown) in the measuring chamber 10'' between its inlets (outlets) 8'' and 9''. These inlets and outlets may be provided with stops 21'' and 22'' corresponding to the stops 21' and 22' in the construction according to FIG. 2. The movement of the measuring element can be measured with the help of any type of a known measuring device, e.g., with the help of a light source and a photocell device in the same manner as in the constructions according to FIGS. 1 and 2. These details have not been marked, however, in FIG. 3. The contstruction in accordance with FIG. 3 has the advantage over that according to FIG. 2, however, that the layout of the lines can be done in a simpler manner. Certain crossing tubes, for example, are not needed.

FIG. 4 shows a double eccentric 23''' which can replace the eccentric 23' according to FIG. 2 or the rocker arm 23'' according to FIG. 3. With the help of the double eccentric 23''', the tubes 4''' and 12''' can thus be clamped together, while at the same time, the tubes 5''' and 13''' are kept open. The compression takes place against the seat 24''' and 25''', respectively.

FIG. 5 finally shows a further embodiment in accordance with the invention. Here too the details substantially correspond to the constructions according to FIGS. 1 to 3. For corresponding parts, the same reference designations have therefore been used but with the addition of the letter a. In the figure, the measuring element is thus marked 10a, and its two inlet or outlet parts are designated 8a and 9a. The flow which is to be measured arrives through an inlet part 1a and is conducted through either of the tubes 4a and 5a, either to the inlet part 8a or the inlet part 9a. After passing through the measuring chamber 10a, the flow is conducted via one of the tubes 12a and 13a to an outlet part 2a. With the help of an eccentric 23a and two lever arms 34a and 35a, either the lines 4a and 12a are shut off, as shown in the figure, or the lines 5a and 13a. Thanks to the lever arms 34a and 35a, a shut-off movement is obtained which is substantially at right angles to the longitudinal direction of the tubes. In this way, a pumping effect is avoided, which otherwise would be brought about owing to the eccentric 23a.

In the position shown in FIG. 5, with the tubes 4a and 12a closed, the liquid measured flows through the tube 5a and causes the float 11a to move towards the left in the figure. The liquid flows further through the duct 36a and the tube 13a up to the outlet part 2a. If, instead, the tubes 5a and 13a are closed and the tubes 4a and 12a are open, the liquid flows instead through the tube 4a, the inlet part 8a, the measuring chamber 10a, and back through the duct 37a, which is connected to the tube 12a, which finally conducts the liquid to the outlet part 2a. Numerals 38a and 39a designate two O-rings between the end part 9a and the measuring chamber 10a. Corresponding O-rings are of course found also in the end part 8a, even though they are not shown in the drawing. The shut off of the different tubes takes place against the seats 24a and 25a, respectively.

It will be clear to those versed in the art that the construction in accordance with FIG. 5 functions in principle in the same manner as those according to FIGS. 1 to 4. The advantages rest in a certain simplification of the tube layout. A further simplification may be achieved if the tubes above the eccentric 23a are joined to a coupling piece corresponding to the coupling piece 27" in FIG. 3.

FIG. 6a illustrates a further simplification of the subject of the invention. In this embodiment, once more the same reference designations have been used as in the earlier figures but with the addition of the letter b. Numeral 1b thus designates an inlet and 2b an outlet. From the inlet 1b, the liquid supplied is introduced into a duct 36b. This duct 36b, together with a corresponding duct 37b on the outlet side, is connected in parallel with the measuring chamber itself. The two ducts and the measuring chamber are arranged jointly to pass through an elongated housing or casing which, as a whole, is designated 10b. This housing is closed at its ends by flexible end walls 8b and 9b. These end walls can be pressed with the help of clamping elements 40b and 41b so as to form a seal against the end openings of the ducts 36b and 37b. This pressing together takes place with the help of four pusher elements 6b, 7b, 14b, and 15b, which thus correspond to the valves 6, 7, 14, and 15 in the embodiment according to FIG. 1.

The function of the embodiment in accordance with FIG. 6a will be substantially the same as the function of the above-described embodiments. It should not be necessary therefore to describe it in greater detail.

Figure 6B:
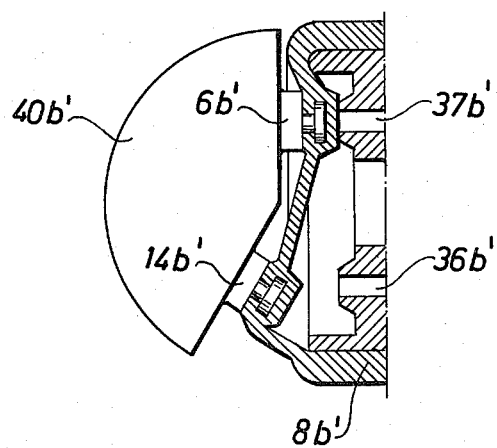

FIG. 6b illustrates a modification of the construction according to FIG. 6a. In this figure, the same reference designations have been used as in FIG. 6a but with the addition of a prime sign. In this case, the pusher elements 6b' and 14b' are attached to the flexible end wall 8b so that in this manner, they positively govern the closing and opening of the end openings on the ducts 36b' and 37b'. As a result, the construction can operate independently of the pressure in these ducts, i.e., at low pressure, as well as at high pressure.

Another possible modification of the construction according to FIG. 6a would be to let the pusher elements 6b, 7b, 14b, and 15b be designed so as to originate from the end walls 8b and 9b. In such a construction, the insertion and/or withdrawal of the measuring chamber housing 10b with its end walls 8b and 9b would be facilitated.

In the above embodiments, constructions have been shown and described in which the time is measured by one photocell device which is measuring the time it takes for the float to pass the photocell, i.e., to travel a certain distance. Of course, it is also possible to use two photocell devices for the measuring of the time it takes for the float to pass the distance between the two photocells.

In the embodiments which have been described, it is the movement of the eccentric or the movement of the rocker arm which decide when the float is to be reversed. Alternatively, the float itself can be made to govern this movement. When the float passes the measuring cell, the voltage in the cell increases, that is to say, a positive slope is obtained which marks the start of measurement. The voltage then remains constant during the further movement of the float. When the float leaves the measuring cell, the voltage in the cell drops and gives rise to a negative slope which marks the finished measurement. Now this negative slope can be made to start a time cycle, which can be fixed or variable, and which influences the movement of the eccentric or of the rocker arm in such a manner that the float is reversed into the desired position. This brings the advantage, among other things, that the space 26' for allowing the liquid to pass by, as shown in FIG. 2 is no longer required. Moreover, the shock pressure, which occurs when the float moves against its stop, or the pressure increase, which occurs when the float comes to a halt in its end position and brakes the liquid, are eliminated.

The invention is intended mainly to be used in connection with the measurement of very small flows, e.g., on the order of magnitude of 1 ml/min. In practice, there is nothing, however, to prevent the principles described to be applied also to the measurement of larger flows.

Naturally, the invention is not limited exclusively to the embodiments described above but may be varied within the scope of the following claims. Different constructions can be obtained, for example, if parts from the different embodiments are exchanged against one another.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A flow meter having an inlet and an outlet for measuring the flow rate of fluid through a conduit, comprising:
   first and second flow paths connected to said inlet, third and fourth flow paths connected to said outlet;
   a measuring chamber including a first port and a second port and including a float disposed therein for movement in first and second directions in response to fluid flow;
   a detector for directly detecting the movement of said float while said float is moving in said first direction or in said second direction in said measuring chamber, so that the time it takes said float to pass said detector while said float is moving in said first direction or said second direction may be measured; and
   means for controlling the path of fluid flow from said inlet to said outlet including operating means movable between first and second positions, whereby in said first position said operating means fluidly connects said first port to said first flow path and fluidly connects said second port to said fourth flow path, and in said second position said operating means fluidly connects said first port to said third flow path and said second port to said second flow path whereby when said operating means is in said first position said fluid is permitted to flow from said inlet through said first and fourth flow paths through said measuring chamber in said first direction so as to move said float in said first direction past said detector, and when said operating means is in said second position said fluid is permitted to flow from said inlet through said second and third flow paths through said measuring chamber in said second direction so as to move said float in said second direction, opposite to said first direction, past said detector.

2. A flow meter in accordance with claim 1 wherein the specific gravity of said float is substantially equal to the specific gravity of the fluid being measured.

3. A flow meter in accordance with claim 1 wherein said float is of a cylindrical shape.

4. A flow meter in accordance with claim 1 wherein said float includes a core and a shell, each having different specific gravities.

5. A flow meter in accordance with claim 1 wherein said measuring chamber is formed from a transparent tube.

6. A flow meter in accordance with claim 1 further including stop members disposed at each end of said measuring chamber to retain said float for a short period of time before the direction of movement of said float is changed.

7. A flow meter in accordance with claim 1 wherein the cross-sectional area at the ends of said measuring chamber is greater than the cross-sectional area at the center of said measuring chamber.

8. A flow meter in accordance with claim 1 wherein said inlet is connected by a Y-junction to said first and second flow paths, and wherein said outlet is connected by a Y-junction to said third and fourth flow paths.

9. A flow meter in accordance with claim 1 wherein said conduit is connected to a four-way valve which is connected to said measuring chamber by said first, second, third, and fourth flow paths.

10. A flow meter having an inlet and an outlet for measuring the flow rate of fluid through a conduit, comprising:
a measuring chamber including a float disposed therein for movement in response to fluid flow;
a detector for detecting the movement of said float in said measuring chamber;
means for controlling the path of fluid flow from said inlet to said outlet including means for allowing fluid to flow from said inlet through said measuring chamber in a first direction so as to move said float in said first direction past said detector, and for allowing fluid to flow from said inlet through said measuring chamber in a second direction so as to move said float in said second direction, opposite to said first direction, past said detector;
said means for allowing fluid to flow including first and second flow paths connected to said inlet, third and fourth flow paths connected to said outlet, and a first port and a second port in said measuring chamber;
said controlling means including operating means for alternately fluidly connecting said first port to one of said first and fourth flow paths and for alternately fluidly connecting said second port to one of said second and third flow paths;
said flow paths being formed of compressible tubes, said operating means operating to compress said tubes to prevent the flow of fluid therethrough; and
means connected to said detector for measuring the rate of fluid flow in response to the movement of said flow in said first and second directions.

11. A flow meter in accordance with claim 10 wherein said operating means for compressing said tubes is an eccentrically-mounted member which is mounted such that it alternately compresses the first and third flow paths and then the second and fourth flow paths against corresponding seats.

12. A flow meter in accordance with claim 11 wherein said operating means further includes lever arms arranged between said eccentric member and said seats to compress said tubes, such that compression takes place substantially at right angles to the axis of said tubes.

13. A flow meter in accordance with claim 10 wherein said operating means is in the form of a rocker arm, the ends of which are movable between two pairs of seats, said rocker arm operating to simultaneously compress the first and third flow paths or the second and fourth paths to prevent the flow of fluid therethrough.

14. A flow meter in accordance with claim 10 wherein said operating means are two members eccentrically mounted and disposed between two seats, said eccentrically-mounted members each operating at the same time to compress one tube against each seat.

15. A flow meter having an inlet and an outlet for measuring the flow rate of fluid through a conduit, comprising:
a measuring chamber including a float disposed therein for movement in response to fluid flow;
a detector for detecting the movement of said float in said measuring chamber;
means for controlling the path of fluid flow from said inlet to said outlet including means for allowing fluid to flow from said inlet through said measuring chamber in a first direction so as to move said float in said first direction past said detector, and for allowing fluid to flow from said inlet through said measuring chamber in a second direction so as to move said float in said second direction, opposite to said first direction, past said detector;
said means for allowing fluid to flow including first and second flow paths connected to said inlet, third and fourth flow paths connected to said outlet, and a first port and a second port in said measuring chamber;
said controlling means including operating means for alternately fluidly connecting said first port to one of said first and fourth flow paths and for alternately fluidly connecting said second port to one of said second and third flow paths;
said first and second flow paths being formed in a first duct and said third and fourth flow paths being formed in a second duct,; and
means connected to said detector for measuring the rate of fluid flow in response to the movement of said float in said first and second directions.

16. A flow meter in accordance with claim 15 wherein said measuring chamber is an elongated housing with flexible end walls which are moved by said operating means against the ends of said first and second ducts.

17. A flow meter in accordance with claim 16 wherein said operating means includes pusher elements for pushing the flexible end walls against the respective end openings of said first and second ducts.

18. A flow meter in accordance with claim 17 wherein said pusher elements are attached to said flexible end walls.

19. A flow meter in accordance with claim 17 wherein said pusher elements are arranged in pairs on said operating means.

* * * * *